United States Patent [19]

Deyerle

[11] Patent Number: 4,671,275
[45] Date of Patent: Jun. 9, 1987

[54] FEMORAL SHAFT SURGICAL RASP FOR USE IN HIP PROSTHESIS SURGERY

[76] Inventor: William M. Deyerle, 1400 Westwood Ave., Richmond, Va. 23227

[21] Appl. No.: 798,807

[22] Filed: Nov. 14, 1985

[51] Int. Cl.[4] ............................................. A61F 17/32
[52] U.S. Cl. ............................... 128/305; 128/92 VJ; 623/23
[58] Field of Search ............... 623/22, 23; 128/92 VJ, 128/305, 305.1, 310

[56] References Cited

U.S. PATENT DOCUMENTS

| | | | |
|---|---|---|---|
| 3,782,373 | 1/1974 | Smythe | 623/23 X |
| 3,814,089 | 6/1974 | Deyerle | 623/23 X |
| 3,815,590 | 6/1974 | Deyerle | 623/23 X |
| 3,815,599 | 6/1974 | Deyerle | 128/305 |
| 4,306,550 | 12/1981 | Forte | 128/92 VJ |
| 4,601,289 | 7/1986 | Chiarizzio et al. | 128/305 |

OTHER PUBLICATIONS

Orthopedic Catalog—Richards Manufacturing Co., Inc., Memphis, TN 38116, USA, 1981, pp. 10, 14, 20.

Primary Examiner—Ronald L. Frinks
Attorney, Agent, or Firm—Mason, Fenwick & Lawrence

[57] ABSTRACT

A femoral shaft surgical rasp for use in performing total and sub-total hip prosthesis surgery to form an elongated canal in an amputated femur shaft for reception of an elongated shank portion of a femoral prosthesis component to be fixed in the canal. The rasp has an elongated handle portion and an elongated working blade portion extending integrally from the handle portion which is a substantial replica of the shank prosthesis component in lateral profile and front and rear elevation. The shank has transverse cross-sections forming a concave sided closed figure based on rectangles corresponding to the rectangular cross-section of the prosthesis shank with four corner edges provided with cutting prominences located at the corners of the basic rectangle and concave side surfaces extending between pairs of corner edges to confine the cutting action of the rasp on the femur to the portions in confronting abutment with said longitudinal edges. A modified version has cutting prominences on two corners and on a convex side opposite the two corners.

6 Claims, 9 Drawing Figures

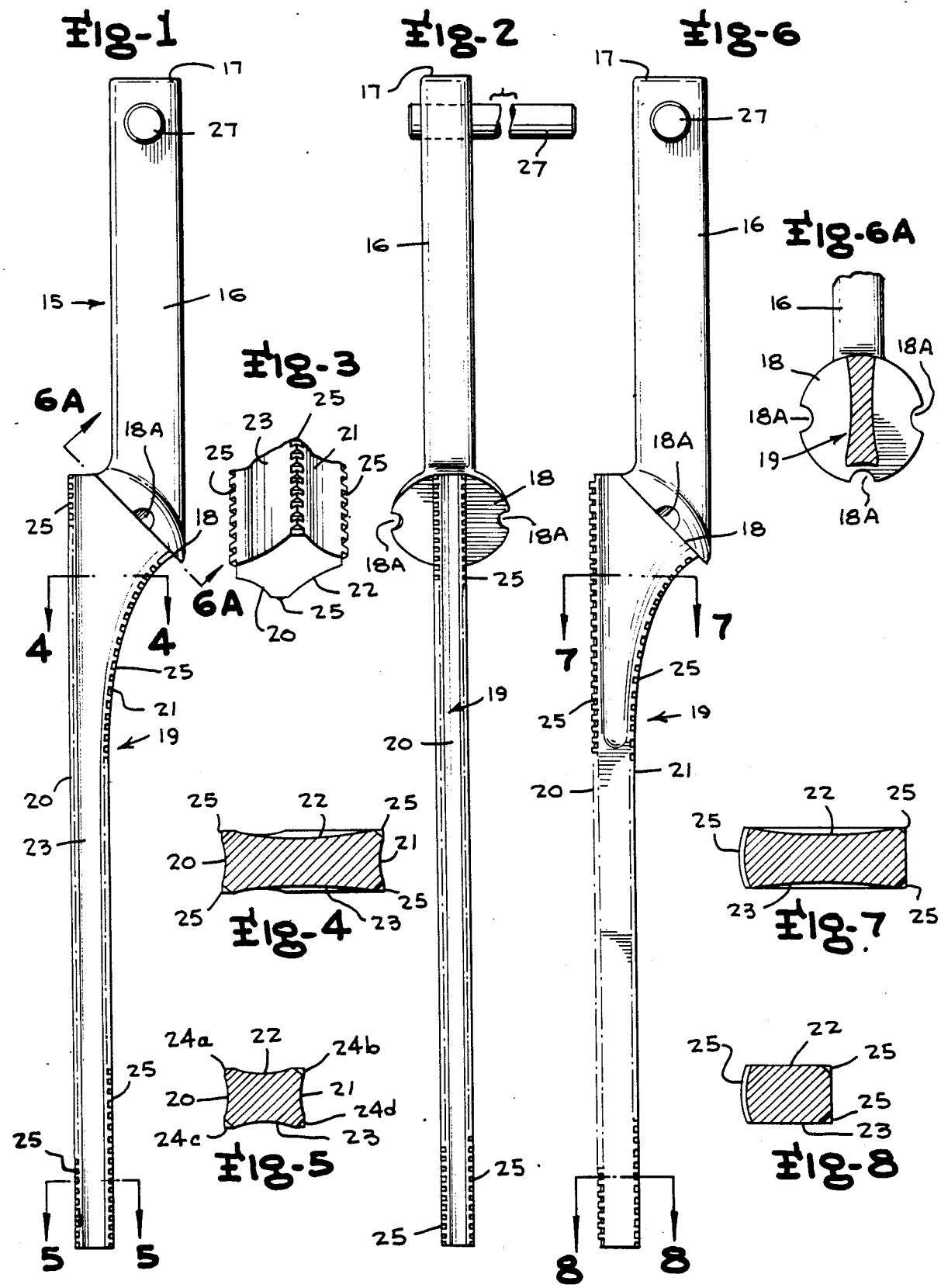

FEMORAL SHAFT SURGICAL RASP FOR USE IN HIP PROSTHESIS SURGERY

BACKGROUND AND OBJECTS OF THE INVENTION

The present invention relates in general to femoral shaft surgical rasps for use in forming an elongated canal in the femoral shaft of the thigh bone after amputation of a portion of the femur, into which a femoral head prosthesis member is inserted and fixed in the course of performing total and subtotal hip prosthesis surgery.

Heretofore, total hip prosthesis surgery has been performed wherein a prosthesis cup is fitted in the acetabulum, and a femoral prosthesis member or head prosthesis member, forming the femoral component of the total prosthesis, which comprises a stem or shank portion and an artificial head, is fixed in the femur shaft to provide a prosthetic hip joint. The fixation of the shank portion of the prosthesis (the head member) in the shaft of the femur has been attempted by forming an appropriately shaped canal or seating recess in the femur shaft and cementing the shank in the femur shaft, or by forming the canal, inserting the prosthesis shank, and drilling and installing bolts transversely through the femur shaft and the prosthesis shank. Considerable difficulties have been encountered in properly forming the canal in the femur for receiving the shank of the femoral portion or head porsthesis member in proper position in the femur shaft with rasps of conventional construction having the cutting prominences on all four surfaces of the rasp as in the case of the typical rasp used in the Harris total hip system (the components of which are advertised and sold by Howmedica, Inc. of Rutherford, N.J.), because of the proximity of soft tissue, such as the abductor muscles, to the path of reciprocative movement of the cutting portion of the rasp. Many surgeons detach the abductors from the greater trochanter to be able to move the abductors away from the path of the rasp so as to avoid damaging them, but the detachment of the abductors adds an aditional approximately six weeks to recuperation time.

Also, previous rasps have the cutting teeth on all four sides and therefore did not allow the surgeon to select the direction of maximum cutting. The direction of this cutting can be critical in proper seating of the prosthesis or trial hip, especially if there has been previous surgery. This is often the case, since many of these total hip prosthesis procedures are done as salvage procedures of old hip with many previous attempts at surgery.

My earlier U.S. Pat. No. 3,815,599 granted June 11, 1974 disclosed a femoral shaft surgical rasp designed to prepare the medullary canal of the femur to receive a shank of a femoral prosthesis member, wherein the rasp blade portion of the surgical rasp conformed generally to the shape of the shaft portion of the femoral prosthesis member, but had cutting prominences along one edge only of the rasping or working portion so as to present smooth surfaces in the other three directions to avoid traumatizing abductor muscles which are still attached to the femur and similar soft tissue. It has been found, however, that it is desirable in many instances to rasp in a manner that will cut only at the corners of the rasp device, preserving the soft cancellous bone to be compressed against the irregular rough surface of the stem of the prosthesis in order to leave bone intact that has a blood supply and provide an ingrowth of bone.

The present state of the art practice is to ream the entire canal out and then force bits of cancellous bone down in beside the eventual stem of the femoral prosthesis member which would be essentially flat or slightly rounded.

I have discovered that it is desirable in many cases to limit the preparatory rasp cuts to the corner of the rasp device cutting portion, so as to leave the soft cancellous bone to be compressed against the stem of the femoral prosthesis device and obviate the necessity of packing bone around the stem, but rather leave bone intact which can compress against the stem of the prosthesis device with bone tissue that has a blood supply. In other words, it is desirable to not disturb the normal blood supply of the soft cancellous bone as it grows into the irregular rough surface of the final inserted stem of the femoral prosthesis device, and thus the four cutting edges of my rasp device are replica for the stem of the prosthesis eventually to be inserted.

An object of the present invention is the provision of a novel femoral shaft surgical rasp construction for use in performing total and subtotal hip prosthesis surgery, wherein the working or rasping portion of the rasp is in the shape of the shaft portion of the femoral prosthesis member to be inserted, and has cutting prominences only along the corners of the working or rasping portion of the rasp with smooth side and end surfaces between the toothed or cutting prominence portions so as to present smooth surfaces along the side faces and end faces of the working or rasping portion of the surgical rasp tool to avoid rasping or cutting the soft cancellous bone confronting those smooth side and end face portions. In this way the soft cancellous bone of the femur or other bone being rasped can be preserved so that it can press against the confronting surface of the shaft of the prosthesis device to be inserted and provide an ingrowth of bone at such confronting portions of the prosthesis shaft.

Other objects, advantages and capabilities of the present invention will become apparent from the following detailed description, taken in conjunction with the accompanying drawing illustrating preferred embodiments of the invention.

BRIEF DESCRIPTION OF THE FIGURES

FIG. 1 is a side elevation view of a preferred embodiment of the femoral shaft surgical rasp device of the present invention having the cutting prominences along only the corners of the working or rasping portion of the rasp device;

FIG. 2 is an end elevation view thereof, viewed from the left hand side of FIG. 1;

FIG. 3 is a fragmentary perspective view of a lower end portion of the working or rasping portion of the rasp device;

FIGS. 4 and 5 are horizontal transverse section views, taken along the lines 4—4 and 5—5 of FIG. 1;

FIG. 6 is a side elevation view of a modified form of the femoral shaft surgical rasp device of the present invention, having one convex toothed surface along the length of the working or rasping portion;

FIG. 6A is a section view taken along the lines 6A—6A of FIG. 1; and

FIGS. 7 and 8 are horizontal transverse section views taken along the lines 7—7 and 8—8 respectively of FIG. 6.

DETAILED DESCRIPTION OF THE PREFERRED EMBODIMENTS

To facilitate understanding of the use of the femoral shaft rasp of the present invention and the advantages of the design, the technique for insertion of the total hip prosthesis by the lateral approach will first be generally reviewed. After the fascia has been opened and the trochanter with its abductor muscles identified, abductors are carefully delineated from the capsule, working from anterior to posterior and posterior to anterior, so that the capsule is separated in its entirety from the abductors. The abductors are left attached to this proximal tip of the trochanter. The proximal tip of the trochanter is carefully osteomotized to avoid any fracture of the distal stock of the femur, which osteotomy may be accomplished with a power saw. A piriformis is frequently attached near the osteotomy site and this is released, and the external rotators which are usually attached partially to the released portion of the trochanter and partially to the distal femur, are individually released. The anterior capsule and the expansion of the origin of the rectus femorus are identified and removed with the cutting cautery. The lateral capsule is separated from the few fibers of the abductor muscles and it also is removed with the cutting cautery. The capsule is delineated carefully from the rectus femorus and the medial portion of the capsule is removed. The posterior capsule is then removed with the cutting cautery.

The head and neck of the femur are removed directly in a transcervical direction by amputation perpendicular to the middle portion of the neck with either a power saw, Gigley saw, or a sharp osteotome, taking care not to fracture the distal stock of the femur. This initial amputation is not necessarily the site of the final seating of the femoral prosthesis but tends to be on the high side just below the cartilage of the femoral head. Using the conventional template for the cup member of the total prosthesis, the position of the cup is checked to see how the cup will seat at at 30° angle. The conventional acetabular index template is used to determine the 30° angle, and the degree of reaming that will be necessary is determined at this point. Making every effort to protect the lateral quarter of inch cartilage in the acetabulum, the cartilages are removed with sharp dissection in the reaming porion of the acetabulum. After the cartilage has been removed, small reamers are used to gradually ream the recipient acetabulum to accept the cup.

The acetabular index template is reinserted at intervals to determine the proper fit for the cup. A template is used to start the slots for the phalanges or spikes on the cup. A sharp instrument is then used to deepend these to appropriate depths. The necessary number of screws for fixing the cup in the acetabulum are then inserted.

Previous orientation with simple prosthesis and cups have tended to err on the side of a loose fit. However, the exact opposite is true with the total hip prosthesis, as an extremely tight fit is essential. In order to obtain a tight fit, an estimate should be made of the amount of the neck of the femur to be removed to obtain this fit. Then slightly less than the estimated amount should be removed in the initial amputation step previously described. This must be done with power instruments in order to avoid fracture. The final amputation site of the neck should then be carefully marked. This may be done with a template in the form of a trial prosthesis template, for example having a removable head corresponding to the head of the actual femoral prosthesis member to be used, and having three holes corresponding to the exact angle of the flange at the base of the neck and head of the prosthesis. The head on the trial template is placed in the acetabulum with the body portion of the template parallel to the femur shaft. An assistant pulls down firmly on the shaft of the femur to give the maximum length for a very tight fit. Drills are inserted through these holes perpendicular to the neck to mark the final amputation site of the neck, and the final amputation is performed with a power saw or osteotome. This is approximately one finger breadth above the lesser trochanter. Prior to the final amputation it is important to identify the most inferior portion of the neck and calcar-femorali and mark it using the cutting cautery. This will usually be found to be slightly anterior to the lesser trochanter and should be marked down to at least as low as the lesser trochanter, regardless of how much neck is removed, the proper line for the inferior edge of the prosthesis will always be visible. This marking may also be accomplished with the use of the burr on an air power instrument.

Prior to any of this surgery in the region of the abductors, a wet lap sheet is placed from the anterior portion of the wound through the posterior portion of the wound around the abductor muscles. This indentifies and protects them throughout the procedure. It is well to have this during the preparation of the acetabular portion also as the wet lap sheet around the deltoid tends to hold moisture in these muscles which could otherwise become dry and have a lowered resistance.

The rasp of the present invention is then used to form the seating recess or canal in the amputated femur shaft. The outline of the insertion of the prosthesis shank is then marked, in the proper plane using the relationship of the right angle tommy bolt 27, and lining it up in relationship to the flexed knee as a method of assaying the proper degree of anteversion. After opening the neck with a box osteotome the rasp is advanced down the canal, continuing to use the right angle marker 27. A curette of smooth instruments may be used to palpate the lining of the canal carefully avoiding any undue disturbance of the cancellous bone. The rasp is inserted at an increasing distance down the canal and then retracted and the canal cleaned out, carefully maintaining the proper version by observing the right angle member 27 (FIG. 2) in its relationship to the flexed knee. In patients with previous surgery, a large amount of cutting at the region of the insertion will be necessary using sharp osteotomes to perform the task. Sharp cutting at this time may avoid the possibility of fracturing either the greater trochanter or the calcar-femorali by attempting to use a rasp in those cases where there is an increase of cortical type bone in the region of the trochanters. This is particularly true in those patients who have had previous surgery, either osteotomies, bone-grafts, or other bony surgery in the region of the hip. An x-ray on the table before closure will avoid a misplacement of any of the components.

The configuration of the femoral component or head member of the total hip prosthesis which is to be installed and fixed in the amputated femur shaft is illustrated in FIG. 1 of the drawings of any earlier U.S. Pat. No. 3,815,599, as an illustrative example, and is indicated in that patent by the reference character 10. The femoral prosthesis member is an integral prosthetic device comprising a head formation, indicated in that patent by reference character 11, having a neck and defining a highly polished spherical head to interfit in the socket defined by the cup member of a total prosthesis. The prosthesis member has an elongated shank or stem portion, shown on that patent at reference character 12, which is substantially flat, extending from the flange formation, there indicated at 13, at the base of the neck of the head formation 11. The shank or stem portion includes a plurality of transverse holes, in that embodiment, extending through the shank or stem near its upper end, which may be about one-quarter inch in diameter, to receive three bolts, for example bolts two inches long of one-quarter inch diameter, designed to extend transversely through the femur shaft and accurately and precisely fix the prosthesis shank in the femur in a manner which effectively resists the torque on the prosthesis head and conveys the stress from the prosthesis member to the hard cortex without either rotary or piston-like motion. The shank of the prosthesis is substantially flat and is of elongated tapering configuration having a straight inner edge, indicated at 12a in that earlier patent, and is substantially concavely tapering outer edge indicated at 12b in that patent.

The rasp to be employed in reaming or forming the canal in the amputated femur shaft for receiving the femoral prosthesis shank, in accordance with the design of the present invention, comprises an elongated rasp member, indicated here by the reference character 15 in FIGS. 1-8, including an elongated handle 16 of generally oval configuration having a butt end 17 and having an enlarged flange 18 at the opposite end of the handle portion disposed at an angle of 45° to the longitudinal axis of the handle 16. Extending below the flange end 18 of the handle 16 is the working portion or cutting portion 19, which has the same configuration as the shank portion of the femoral prosthesis member, in lateral profile, defining a straight back edge 20 and a concavely curved front edge 21. The straight back edge 20 of the working portion 19, and the concavely curved front edge 21 of this working portion 19, as well as the two opposite side portions 22 and 23, are each slightly concavely curved as shown best in the section views FIGS. 4 and 5 and also as is apparent from the fragmentary perpective section FIG. 3. The corner or juncture portions 24a, 24b, 24c and 24d are formed with teeth or cutting prominences, indicated at 25, along the length thereof. The working portion 19 of the rasp 15 is progressively inserted at increasing distances down the canal to be formed in the amputated femur shaft and is then retracted, until the canal is formed to a sufficient depth to permit full seating of the rasp and finally the femoral prosthesis shaft therein. Because the smooth concave surface portion 20, 21, 22, and 23 of the working or cutting portion 19 between the corner-located teeth or cutting prominences 25 are smooth, there are no teeth directly confronting the very important abductors which remain attached to the greater trochanter so that chewing up, damaging or traumatizing of these abductors may be avoided, while leaving some cancellous bone along the side and end surfaces confronting the concave sides and ends. Furthermore, the rasp cuts much more efficiently, because the smooth edges of the concave surface portions 20-23 do not present resistance to cutting action by the limited area or zones occupied by the teeth 25 at the corners of the working portion 19. Also, since the cutting prominences 25 occupy only limited zones at the corners, the rasp has much higher efficiency than a normal rasp having cutting teeth on both the straight surfaces 20 and concave surfaces 21 of the working portion 19 which would be the customary design, since the operator does not have to overcome the resistance to cutting offered by the bone portions contacting the smooth portions of the rasp. Efficiency is also improved somewhat because bone surfaces against which the smooth concave portions 20-23 work assist in forcing the teeth at the corner portions into cutting engagement with the bone surface portions engaged by the teeth.

The modified form of the surgical rasp shown in FIGS. 6, 7 and includes an elongated handle 16 of generally oval configuration and abut end 17 and enlarged flange end 18, like the rasp shown in FIGS. 1-5. Extending below the flange end 18 of the handle 16 is the working or cutting portion 19 of the rasp, which has the same configuration as the shank portion of the femoral prosthesis member, in lateral profile, defining a straight back edge 20, which in this version is of slightly convex cross-sectional configuration, while the opposite edge of the rasp, when viewed in profile, has a convexly curved configuration indicated at 21. The two opposite side portions 22 and 23 of the rasp cutting portion 19 in this version are of slightly concave configuration in the upper regions thereof, as shown by the cross-section view of FIG. 7 and the sides merge into a flat configuration at the lower end portion as shown in FIG. 8. The corners of the juncture portions 24b and 24d in this version are formed with teeth or cutting prominences, indicated at 25, along the length thereof, corresponding to the teeth or cutting prominences 24b, 24d of the FIGS. 1-5 version, and the straight back edge 20 has teeth 25' which extend entirely from one side to the other of the rasp cutting portion 19 along the convex surface thereof.

After forming of the canal in the amputated femur shaft by use of the rasp 15, a jig and femoral prosthesis member or replica are positioned relative to the femur to guide drill bits to form drill holes transversely in the femur for fixation bolts to fix the prosthesis in position. The jig which may be of the type disclosed in my U.S. Pat. No. 3,814,089 issued June 4, 1974, may be attached to the femoral prosthesis member, after which the shank of the femoral prosthesis member is inserted in the canal to substantially the proper position. In either case, holes are drilled transversely through the femur shaft by inserting the drill through the guide holes in the guide leg of the jig and through the holes in the replica of the femoral prosthesis shank or through the holes in the prosthesis shank to which the jig is attached, in the manner described in that earlier patent. After the drill holes are formed, and the shank of the femoral prosthesis member is tapped into place and the holes in the prosthesis shank accurately lined up with the holes drilled in the femur shaft, bolts, such as one-forth inch diameter bolts approximately 2 inches along or 1¾ inch having hexagonal heads, are driven into the proximal cortex and into the deep cortex to fix the femoral prosthesis member. After the femoral prosthesis component has been fixed in the femur, and assuming the prosthesis cup has been fixed in place in the acetabulum, strong traction is applied and, with the aid of a nylon end concave prosthesis inserter, the head of the femoral prosthesis is pushed into the prosthesis cup, tests are conducted to see that the leg has a proper range of movement and the wound is closed.

The hereinabove described rasp facilitates the formation of an approximately sized and configured channel corresponding substantially in cross-section and in profile to the stem or shank portion of the femoral prosthesis member in a most efficient manner, providing an accurate fit of the femoral prosthesis member shank in the thus formed canal in the femur shaft. The femoral prosthesis member can then be accurately and rigidly fixed in the femur shaft, for example by the method disclosed in my tow earlier above identified patents, with bolts being inserted through the transverse bolt holes formed by the method disclosed in those applications. This makes absolute fixation of the prosthesis member possible without the use of methyl merthacrylate cement, as has been frequently used in the past, but which has been discovered to present a serious hazard to the patient. Also, the presence of previous infection in the femur of the patient effectively precludes the use of methyl merthacrylate bone cement, whereas use of my fixation technique involving formation of the accurately sized canal for the femoral prosthesis member shank accurately sized by the above-described rasp and fixed in position by transverse bolts allows use of the total hip prosthesis procedure for such patients.

A careful preservation of a cancellous bone left by the concave rasp is accomplished by inserting a constant version angle which is accurately identified by the angle of the 7 inch member shown in FIGS. 1 and 2 and 6, identified by reference character 27. The relationship of this 7 inch reduction angle bar 27 to the flexed knee determines accurately the amount of anterversion or absence thereof of the inserted prosthesis to the femur. This will allow the eventual insertion of the prosthesis to be evaluated in the same manner by reduction lever attached to the prosthesis as it is inserted.

The calcar flange 18 is a replica of the eventual calcar flange on the prosthesis to be inserted. In order to assure accurate seating and placing of the amputated calcar and neck, three holes are provided in the periphery of flange 18, illustrated in FIGS. 1, 2 and 6 at 18A. The slots 18A allow for the visual perception of a careful press-fit of the calcar flange down on the calcar and the neck. These slots are identical with those on the eventual to-be-inserted stem, to ascertain a proper fit, of the flange on the calcar at the final seating.

All the above features are aimed at preserving as much cancellous bone stock and accurately inserting of both the rasp and eventual prosthesis, exact same depth, and amount of version, thus giving better fixation and ingrowth.

I CLAIM:

1. A femoral shaft surgical rasp for use in performing total and sub-total hip prosthesis surgery to form an elongated canal in an amputated femur shaft for reception of an elongated shank portion of a femoral prosthesis component to be fixed in the canal, the femoral prosthesis component having a head portion integral with the shank portion including a flanged neck at the juncture of the head and shank portions and the shank portion having rectangular transverse cross-sections throughout with substantially flat longitudinal sides including straight longitudinal side and an opposite side extending longitudinally along a concavely curving path along at least part of its length, the rasp comprising an elongated handle portion and an elongated working blade portion extending integrally from the handle portion which is a substantial replica of the prosthesis member shank in lateral profile and front and rear elevation having its transverse cross-sections forming a concave sided closing figure base on rectangles corresponding to the rectangular cross-sections of the prosthesis stem with four corner edges located at the corners of the basic rectangle and concave side surfaces extending between pairs of corner edges, the rasp having cutting prominences only along corner edges thereof to confine the cutting action of the rasp on the femur to the portions in confronting abutment with said longitudinal edges, and the concave side surfaces between the longitudinal edges preserving the soft cancellous bone to be compressed against said flat longitudinal sides of the prosthesis stem so as to leave bone intact that has a blood supply and provides an ingrowth of bone.

2. A femur shaft surgical rasp as defined in claim 1, wherein said elongated handle portion and said working portion extend along parallel axes in opposite directions from the juncture theebetween.

3. A femur shaft surgical rasp as defined in claim 1, wherein said rasp includes a flanged calcar collar formation at the juncture of said handle and working portions which substantially duplicates relative to the axis of said working portion the angular disposition of said flanged neck of the prosthesis component relative to the longitudinal axis of prosthesis shank and presents a flat substantially encircling inclined surface toward the working portion simulating the surface of the flanged neck facing toward the prosthesis shank.

4. A femur shaft surgical rasp as defined in claim 2, wherein said rasp includes a flanged collar formation at the juncture of said handle and working portions which substantially duplicates relative to the axis of said working portion the angular disposition of said flanged neck of the prosthesis component relative to the longitudinal axis of the prosthesis shank and presents a flat substantially encircling inclined surface toward the working portion simulating the surface of the flanged neck facing toward the prosthesis shank.

5. A femur shaft surgical rasp as defined in claim 1, wherein said cutting prominences are located on all four of said longitudinal corner edges of said working portion of the rasp along the entire length thereof.

6. A femoral shaft surgical rasp for use in performing total and sub-total hip prosthesis surgery to form an elongated canal in an amputated femur shaft for reception of an elongated shank portion of a femoral prosthesis component to be fixed in the canal, the femoral prosthesis component having a head portion intergral with the shank portion including a flanged neck at the juncture of the head and shank portions and the shank portion having rectangular transverse cross-section throughout with substantially flat longitudinal sides including straight longitudinal side and an opposite side extending longitudinally along a concave curing path along at least part of its length, the rasp comprising an elongated handle portion and an elongated working blade portion extending integrally from the handle portion which is a substantial replica of the prosthesis member shank in lateral profile and front and rear elevation having its transverse cross-sections forming a concave sided closed figure based on rectangles corresponding to the rectangular cross-sections of the prosthesis stem with four corner edges located at the corners of the basic rectangle and having concave side surfaces extending between corner edges at three sides of the blade portion, the rasp having cutting prominences only along a pair of corner edges thereof at junctures of said three sides to confine the cutting action of the rasp on the femur to the portions in confronting abutment with said longitudinal edges, and the concave side surfaces between the longitudinal edges preserving the soft cancellous bone to be compressed against said flat longitudinal sides of the prosthesis stem so as to leave bone intact that has a blood supply and provides an ingrowth of bone, and said blade portion having a fourth side opposite the side extending between said corner edges having cutting prominences transversely spanning the width of said fourth side and occurring along the entire length thereof.

* * * * *